US00PP23983P3

(12) United States Plant Patent
Zaiger et al.

(10) Patent No.: US PP23,983 P3
(45) Date of Patent: Oct. 15, 2013

(54) INTERSPECIFIC TREE NAMED 'SUNSET DELIGHT'

(50) Latin Name: *Prunus*
Varietal Denomination: SUNSET DELIGHT

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 93 days.

(21) Appl. No.: 13/385,300

(22) Filed: Feb. 13, 2012

(65) Prior Publication Data

US 2013/0212753 P1 Aug. 15, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

| | | | | |
|---|---|---|---|---|
| PP12,409 | P2 * | 2/2002 | Zaiger et al. | Plt./180 |
| PP13,134 | P2 * | 10/2002 | Zaiger et al. | Plt./184 |
| PP13,526 | P2 * | 1/2003 | Zaiger et al. | Plt./180 |
| PP23,106 | P2 * | 10/2012 | Zaiger et al. | Plt./180 |

* cited by examiner

*Primary Examiner* — Wendy C Haas

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with very good flavor and eating quality.
2. Fruit with an attractive red-yellow skin color.
3. Fruit with good handling and shipping quality.
4. Fruit with an average Brix of 18.5° and a good balance between acid and sugar.
5. Heavy and regular bearer of large size fruit.
6. Vigorous, upright tree growth.

1 Drawing Sheet

Botanical designation: Interspecific *Prunus* species.
Variety denomination: 'SUNSET DELIGHT'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of interspecifics, peaches and nectarines, which are known to us, and mentioned herein, 'Dapple Fire' Interspecific (U.S. Plant Pat. No. 12,409), the proprietary interspecific plum seedlings '22M137', '52MB278' and '338LN1', the proprietary genetic dwarf nectarine '182GE276' and the interspecific genetic dwarf nectarine '332LH358', all of which are non-patented.

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species; *Prunus salicina*, *Prunus persica* var. *nucipersica* and *Prunus persica*. The present variety was originated by us as a first generation cross between the proprietary non-patented interspecific seedlings '22M137' and '52MB278'. The seed parent '22M137' (non-patented) originated as a first generation cross between the following varieties; 'Dapple Fire' Interspecific (U.S. Plant Pat. No. 12,409) and the proprietary genetic dwarf nectarine seedling '182GE276' (non-patented). The pollen parent '52MB278' (non-patented) originated as a first generation seedling from the cross of our proprietary interspecific plum seedling selection '338LN1' (non-patented) with the proprietary interspecific genetic dwarf nectarine seedling '332LH358' (non-patented). We budded a large number of these seedlings to older 'Nemaguard' Rootstock (non-patented) trees to induce earlier fruit production for evaluation. Under close and careful observation, one such seedling, which is the present variety, exhibited desirable fruit and tree characteristics and was selected in 2008 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree, which includes peaches, nectarines and interspecifics in its parentage, is of large size, vigorous upright growth and a productive and regular bearer of large size, yellow flesh fruit with very good flavor and eating quality. The fruit is further characterized by having firm flesh, an attractive red-yellow skin color and having good storage and shipping quality. In comparison to its seed parent '22M137' (non-patented) the fruit of the new variety has skin that is mostly red skin compared to yellow-orange skin and is approximately 23 days later in maturity. In comparison to its pollen parent '52MB278' (non-patented) the fruit of the new variety has red-yellow skin compared to green and is approximately 21 days later in maturity. In comparison to the commercial interspecific variety 'Black Kat' (U.S. Plant Pat. No. 13,134) the fruit of the new variety has red-yellow skin compared to black and is approximately 4 days later in maturity. In comparison to its ancestor 'Dapple Fire' (U.S. Plant Pat. No. 12,409) the fruit of the new variety has yellow flesh compared to red and is approximately 68 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color.

Tree:

- *Size*.—Large, pruned to 3 to 3.5 meters in height and width for economical harvesting of fruit. Varies with different cultural practices.
- *Vigor*.—Vigorous, growth of 1.5 to 2 meters the first growing season. Varies slightly with type and fertility of soil, climatic conditions and cultural practices.
- *Form*.—Upright, usually pruned to vase shape to allow more sunlight to center of tree to enhance fruit color and health of fruit spurs.
- *Branching habit*.—Upright, crotch angle approximately 25°, increases with heavy crop load.
- *Productivity*.—Productive, thinning and spacing of fruit necessary for desired market size. Fruit set varies with climatic conditions during blooming season.
- *Bearer*.—Regular, adequate fruit set 3 consecutive years. No alternate bearing observed.
- *Fertility*.—Self sterile, pollinator required.
- *Density*.—Medium dense, controlled by pruning.
- *Hardiness*.—Hardy in all stone fruit growing areas of California. Tree grown in USDA Hardiness Zone 9. Winter chilling requirement approximately 800 hours at or below 45° F.

Trunk:

- *Size*.—Medium. Average circumference of 40.6 cm at 27.9 cm above ground on a 5 year old tree.
- *Stocky*.—Medium stocky.
- *Texture*.—Medium shaggy, roughness increases with age of tree.
- *Color*.—Varies from 10YR 2/2 to 2.5Y 5/2.

Branches:

- *Size*.—Medium. Average circumference 8.8 cm at 1.0 meter above ground. Crotch angle approximately 25°, increases with heavy crop load.
- *Surface texture*.—New growth relatively smooth. Mature growth medium rough, roughness increases with age.
- *Lenticels*.—Size — medium. Average number 37 in a 25.8 sq cm section. Average length 3.9 mm. Average width 1.3 mm. Color varies from 10YR 5/10 to 7.5YR 5/10.
- *Color*.—New growth 5GY 4/8. Mature growth varies from 7.5YR 2/2 to 10YR 2/2, varies with age of growth.

Leaves:

- *Size*.—Medium. Average length 78.3 mm. Average width 31.7 mm.
- *Form*.—Oblanceolate.
- *Apex*.—Acuminate.
- *Base*.—Cuneate.
- *Margin*.—Serrate.
- *Thickness*.—Medium.
- *Surface texture*.—Upper surface relatively smooth, slight indentations over midrib and leaf veins. Lower surface relatively smooth, except for small ridges created by midrib and pinnate venation. Both surfaces glabrous.
- *Petiole*.—Medium. Average length 13.9 mm. Average width 1.4 mm. Longitudinally grooved. Surface — glabrous. Color 5GY 5/6.
- *Glands*.—Type — globose. Size — small. Average length 1.1 mm. Average diameter 0.3 mm. Average number 2, varies from 2 to 4. Located primarily on the upper portion of the petiole and the base of the leaf blade. Color 5GY 6/6.
- *Stipules*.—Average number 2. Average length 4.3 mm. Margin — pectinate. Color varies from 5GY 6/6 to 5GY 5/6.
- *Color*.—Upper surface varies from 5GY 2/2 to 7.5GY 2/4. Lower surface varies from 7.5GY 4/2 to 10GY 3/2. Midvein color varies from 5GY 7/6 to 5GY 6/6.

Flower buds:

- *Size*.—Small to medium. Average length 9.7 mm. Average width 5.6 mm.
- *Hardiness*.—Hardy with respect to California winters.
- *Form*.—Plump, conical becoming elongated as it matures.
- *Pedicel*.—Medium. Average length 7.4 mm. Average width 0.8 mm. Color varies from 2.5GY 7/6 to 2.5GY 7/8. Surface — glabrous.
- *Color*.—N 9.5/ (white).
- *Number of buds per spur*.—Average 10, varies from 7 to 12. Varies with age of spur.

Flowers:

- *Blooming period*.—Date of First Bloom — Feb. 22, 2011. Date of Petal Fall — Mar. 2, 2011, varies slightly with climatic conditions.

*Size*.—Medium. Average height 11.6 mm. Average diameter 18.4 mm.

*Petals*.—Normally 5, alternately arranged to sepals. Size — small. Average length 8.8 mm. Average width 7.3 mm. Form — obovate. Margin — sinuate. Both upper and lower surfaces glabrous. Color — N 9.5/ (white).

*Sepals*.—Normally 5, alternately arranged to petals. Size — small. Average length 3.2 mm. Average width 2.7 mm. Shape — triangular, apex rounded. Margin — entire. Both upper and lower surfaces glabrous. Color — upper surface varies from 2.5GY 7/6 to 5GY 7/6. Lower surface varies from 2.5GY 6/6 to 5R 3/8.

*Stamens*.—Average number per flower 32. Average filament length 8.2 mm. Filament color N 9.5/ (white). Anther color varies from 2.5Y 8/10 to 5Y 8/10.

*Pollen*.—Present, self sterile, pollinator required. Color varies from 2.5Y 7/12 to 2.5Y 6/10.

*Pistil*.—Normally one. Surface — glabrous. Average length 9.2 mm. Position of stigma average of 1.3 mm below anthers. Color varies from 2.5GY 8/8 to 2.5GY 7/6.

*Fragrance*.—Heavy aroma.

*Color*.—N 9.5/ (white).

*Number flower per flower bud*.—Average 2, varies from 1 to 3.

*Pedicel*.—Average length 8.3 mm. Average width 0.9 mm. Color varies from 2.5GY 7/6 to 2.5GY 7/8.

Fruit:

*Maturity when described*.—Firm ripe.

*Date of first picking*.—Sep. 8, 2011.

*Date of last picking*.—Sep. 17, 2011, varies slightly with climatic conditions.

*Size*.—Large. Average diameter axially 70.4 mm. Average transversely in suture plane 62.3 mm. Average weight 181.8 grams varies slightly with fertility of the soil, amount of thinning and climatic conditions.

*Form*.—Globose to slightly elongated.

*Suture*.—Lipped, extends from base to apex.

*Ventral surface*.—Slightly lipped.

*Apex*.—Flat to very slightly rounded.

*Base*.—Flat.

*Stem cavity*.—Rounded to slightly elongated in suture plane. Average depth 8.0 mm. Average diameter 3.1 mm.

Stem:

*Size*.—Medium. Average length 13.2 mm. Average diameter 2.2 mm.

*Color*.—Varies from 10Y 6/6 to 10Y 7/8.

Flesh:

*Ripens*.—Evenly.

*Texture*.—Firm, meaty, crisp.

*Fibers*.—Few, very small, tender.

*Firmness*.—Firm, comparable to the commercial interspecific 'Black Kat' (U.S. Plant Pat. No. 13,134).

*Aroma*.—Moderate aroma.

*Amydgalin*.—Undetected.

*Eating quality*.—Very good.

*Flavor*.—Very good, good balance between acid and sugar.

*Juice*.—Moderate amount, enhances flavor.

*Brix*.—Average Brix 18.5°, varies slightly with amount of fruit per tree and climatic conditions.

*Color*.—Varies from 10YR 7/8 to 2.5Y 8/6.

*Pit cavity*.—Average length 33.4 mm. Average width 20.0 mm. Average depth 5.2 mm. Color varies from 7.5YR 5/8 to 10YR 6/6.

Skin:

*Thickness*.—Medium.

*Surface*.—Smooth.

*Bloom*.—Moderate amount.

*Tendency to crack*.—None.

*Color*.—Ground color varies from 2.5Y 7/8 to 2.5Y 8.5/4. Overspread with 7.5R 2/6 to 5R 3/8.

*Tenacity*.—Tenacious to flesh.

*Astringency*.—Undetected.

Stone:

*Type*.—Clingstone.

*Size*.—Large. Average length 32.7 mm. Average width 19.4 mm. Average thickness 8.7 mm.

*Form*.—Obovoid.

*Base*.—Relatively flat.

*Apex*.—Pointed. Average length 1.2 mm.

*Surface*.—Very small pits throughout.

*Sides*.—Unequal, one side extending further outward from the suture plane.

*Ridges*.—A small narrow ridge on each side of suture extending from base toward apex.

*Tendency to split*.—None.

*Color*.—Varies from 10YR 6/8 to 10YR 7/8 when dry.

Kernel:

*Size*.—Medium. Average length 16.3 mm. Average width 10.4 mm. Average depth 5.0 mm.

*Form*.—Ovoid.

*Viability*.—Viable, complete embryo development.

*Skin*.—Color varies from 2.5Y 8/6 to 2.5Y 7/6.

Use:

*Dessert*.—Market — local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

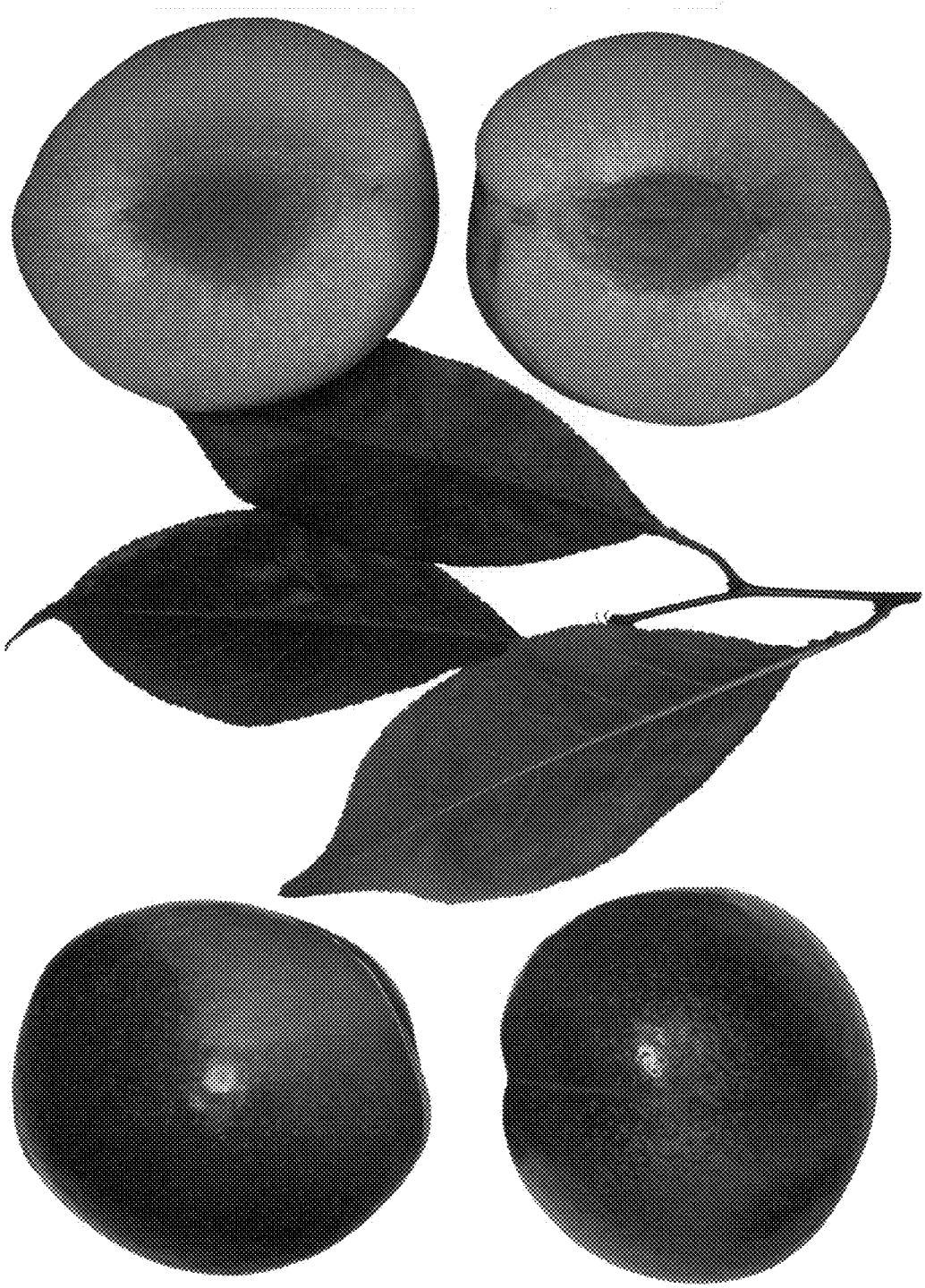

* * * * *